United States Patent
Kaneda et al.

(10) Patent No.: US 7,462,604 B2
(45) Date of Patent: Dec. 9, 2008

(54) HAIR GROWTH PROMOTOR COMPOSITION

(75) Inventors: Sumi Kaneda, Sumida-ku (JP);
Nobuyasu Satou, Sumida-ku (JP);
Masatoshi Hasegawa, Sumida-ku (JP);
Masahiro Motono, Onojo (JP)

(73) Assignees: Lion Corporation, Tokyo (JP); Sansho Seiyaku Co., Ltd., Fukuoka (JP)

( * ) Notice: Subject to any disclaimer, the term of this patent is extended or adjusted under 35 U.S.C. 154(b) by 198 days.

(21) Appl. No.: 10/573,994

(22) PCT Filed: Sep. 29, 2004

(86) PCT No.: PCT/JP2004/014269

§ 371 (c)(1),
(2), (4) Date: Mar. 30, 2006

(87) PCT Pub. No.: WO2005/030152

PCT Pub. Date: Apr. 7, 2005

(65) Prior Publication Data

US 2007/0116657 A1    May 24, 2007

(30) Foreign Application Priority Data

Sep. 30, 2003    (JP)    ............ 2003-340304

(51) Int. Cl.
A01N 43/04    (2006.01)
A61K 31/70    (2006.01)
(52) U.S. Cl. ............ 514/45; 514/43; 514/46; 514/47
(58) Field of Classification Search .......... None
See application file for complete search history.

(56) References Cited

U.S. PATENT DOCUMENTS

| | | | |
|---|---|---|---|
| 4,745,103 A | 5/1988 | Oono et al. | |
| 5,656,264 A | 8/1997 | Hanada et al. | |

FOREIGN PATENT DOCUMENTS

| | | | |
|---|---|---|---|
| JP | 61-15815 A | 1/1986 | |
| JP | 02-37886 | 8/1990 | |
| JP | 3-261708 A | 11/1991 | |
| JP | 05-320028 | 12/1993 | |
| JP | 07-233037 | 9/1995 | |
| JP | 10-72321 A | 3/1998 | |
| JP | 11322545 A | 11/1999 | |
| JP | 2001-26520 A | 1/2001 | |
| JP | 2003-155218 A | 5/2003 | |

OTHER PUBLICATIONS

International Report on Patentability (Form PCT/IB/338 and 373)/Written Opinion of the International Searching Authority (Form PCT/ISA/237), Jun. 29, 2006, PCT/JP2004/014269, Geneva, Switzerland.
XP002455643, Database Chemical Abstracts, Accession No. 131:355901.
XP002455645, Database WPI Week 199821, Derwent Publications Ltd., London, GB; AN 1998-234678.

*Primary Examiner*—Patrick T Lewis
(74) *Attorney, Agent, or Firm*—Buchanan Ingersoll & Rooney PC

(57) ABSTRACT

A hair growth promotor which is an ethanol or aqueous ethanol preparation comprising, as active ingredients for a hair growth promotor, (A) at least one compound selected from fatty acids having a chain length of an odd number of carbon atoms, the derivatives of the fatty acids, aliphatic alcohols having a chain length of an odd number of carbon atoms and the derivatives of the aliphatic alcohols and (B) at least one selected from 6-benzylaminopurine and/or the derivatives thereof represented by the following Formula (I), wherein it further comprises (C) at least one of polyglycerin fatty acid esters and (D) at least one of sorbitan fatty acid esters:

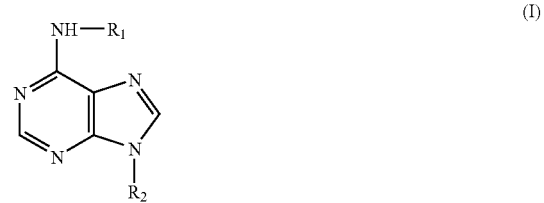

(I)

in Formula (I), $R_1$ and $R_2$ are defined. The hair growth promotor can have an excellent hair growth effect and can provide an excellent stabilization effect at low temperature and can provide good feeling having no stickiness.

1 Claim, No Drawings

HAIR GROWTH PROMOTOR COMPOSITION

TECHNICAL FIELD

The present invention relates to a hair growth promotor composition, more specifically to a hair growth promotor composition which improves dissolution stability of a preparation by containing a specific solubilizing agent and which effectively exhibits a hair growth effect by active ingredients.

BACKGROUND ART

6-Benzylaminopurine(6-benzyladenine) and derivatives thereof have so far been known as an external preparation having the purposes of an antiaging effect for a skin and activation of cells by applying externally onto a scalp (refer to, for example, patent document 1). Further, it is known that an excellent hair growth effect is obtained by using 6-benzylaminopurine and derivatives thereof and fatty acids having a chain length of an odd number of carbon atoms and derivatives thereof in combination (refer to, for example, patent document 2).

Further, it is known as well that nonionic surfactants having an HLB value of 10 or less are effective for dissolving fatty acids having a chain length of an odd number of carbon atoms and derivatives thereof (refer to, for example, patent document 3).

On the other hand, it is known as well that polyhydric alcohols are effective as a solubilizing agent for 6-benzylaminopurine (refer to, for example, patent document 4).

However, it is difficult to stabilize dissolution of a preparation in which 6-benzylaminopurine and derivatives thereof are coexistent with fatty acids having a chain length of an odd number of carbon atoms and derivatives thereof, and in particular, the problem that active ingredients in the preparation are deposited at low temperature is involved therein. Accordingly, the stability at low temperature is not yet satisfactory in terms of actual use, and the existing situation is that hair growth promotor compositions having further excellent dissolution stability are still desired.

Patent document 1: Japanese Patent Application Laid-Open No. 320028/1993 (claims, examples and other)
Patent document 2: Japanese Patent Application Laid-Open No. 233037/1995 (claims, examples and other)
Patent document 3: Japanese Patent publication No. 37886/1990 (claims, examples and other)
Patent document 4: Japanese Patent Application Laid-Open No. 72321/1998 (claims, examples and other)

DISCLOSURE OF THE INVENTION

In light of the problems of the prior art described above and the existing situation, the present invention intends to solve them, and an object thereof is to provide a hair growth promotor composition which provides an excellent hair growth effect by applying externally onto a scalp and which is excellent particularly in stability at low temperature and has a good use feeling.

Intensive researches repeated by the present inventors in order to solve the conventional problems described above have resulted in finding that a hair growth promotor composition which meets the object described above and which is excellent in stability at low temperature is obtained when containing at least one compound selected from fatty acids having a chain length of an odd number of carbon atoms, the derivatives of the fatty acids, aliphatic alcohols having a chain length of an odd number of carbon atoms and the derivatives of the aliphatic alcohols, 6-benzylaminopurine and/or a derivative thereof and two kinds of fatty acid esters, and thus the present invention has come to be completed.

That is, the hair growth promotor composition of the present invention is an ethanol or aqueous ethanol preparation comprising, as active ingredients for a hair growth promotor, (A) at least one compound selected from fatty acids having a chain length of an odd number of carbon atoms, the derivatives of said fatty acids, aliphatic alcohols having a chain length of an odd number of carbon atoms and the derivatives of said aliphatic alcohols and (B) at least one selected from 6-benzylaminopurine and/or the derivatives thereof represented by the following Formula (I), wherein it further comprises (C) at least one of polyglycerin fatty acid esters and (D) at least one of sorbitan fatty acid esters:

in Formula (I), $R_1$ is an alkyl group having 1 to 22 carbon atoms, a cyclic hydrocarbon group, an alkenyl group having 1 to 22 carbon atoms, an aralkyl group which is non-substituted or has a substituent, a styryl group which is non-substituted or has a substituent, an alkylamino group, an amino group having a cyclic hydrocarbon group, an alkenylamino group, a benzylamino group which is non-substituted or has a substituent, a phenylethylamino group which is non-substituted or has a substituent, a phenylamino group which is non-substituted or has a substituent, a phenylaminocarbonylamino group which is non-substituted or has a substituent, a pyridylamino group, a pyridylmethylamino group, a pyrrolylmethylamino group, an oxazolylmethylamino group, an imidazolylmethylamino group, a pyridazolylmethylamino group, a naphthylamino group or a naphthylmethylamino group, and $R_2$ is a hydrogen atom, a pentose or hexose.

EFFECTS OF THE INVENTION

According to the present invention, provided is a hair growth promotor composition which has an excellent hair growing effect and provides an excellent stabilization effect at low temperature and which provides a good use feeling having no stickiness.

BEST MODE FOR CARRYING OUT THE INVENTION

The embodiment of the present invention shall be explained below in details.

The hair growth promotor composition of the present invention is an ethanol or aqueous ethanol preparation comprising, as active ingredients for a hair growth promotor, (A) at least one compound selected from fatty acids having a chain length of an odd number of carbon atoms, the derivatives of said fatty acids, aliphatic alcohols having a chain length of an odd number of carbon atoms and the derivatives of said aliphatic alcohols and (B) at least one selected from 6-benzylaminopurine and/or the derivatives thereof represented by the following Formula (I), wherein it further comprises (C) at least one of polyglycerin fatty acid esters and (D) at least one of sorbitan fatty acid esters:

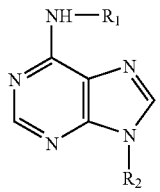
(I)

in Formula (I), $R_1$ is an alkyl group having 1 to 22 carbon atoms, a cyclic hydrocarbon group, an alkenyl group having 1 to 22 carbon atoms, an aralkyl group which is non-substituted or has a substituent, a styryl group which is non-substituted or has a substituent, an alkylamino group, an amino group having a cyclic hydrocarbon group, an alkenylamino group, a benzylamino group which is non-substituted or has a substituent, a phenylethylamino group which is non-substituted or has a substituent, a phenylamino group which is non-substituted or has a substituent, a phenylaminocarbonylamino group which is non-substituted or has a substituent, a pyridylamino group, a pyridylmethylamino group, a pyrrolylmethylamino group, an oxazolylmethylamino group, an imidazolylmethylamino group, a pyridazolylmethylamino group, a naphthylamino group or a naphthylmethylamino group, and $R_2$ is a hydrogen atom, a pentose or hexose.

In the present invention, the fatty acid having a chain length of an odd number of carbon atoms which is used as the component (A) may be saturated fatty acid or unsaturated fatty acid as long as it has an odd number of carbon atoms constituting the carbon chain and has a hair growth action.

The unsaturated fatty acid may contain plural double bonds. The carbon chain has preferably 9 to 29 carbon atoms, more preferably 11 to 25 carbon atoms, and the carbon chain may be linear or branched. To be more specific, capable of being given as such a fatty acid are, for example, nonanoic acid, undecanoic acid, tridecanoic acid, pentadecanoic acid, nonadecanoic acid, heneicosanoic acid, tricosanoic acid, pentacosanoic acid and heptacosanoic acid.

Any derivatives of the fatty acids having a chain length of an odd number of carbon atoms described above can be used as the usable derivatives of the fatty acids having a chain length of an odd number of carbon atoms as long as they contain fatty acid residues of fatty acids having an odd number of carbon atoms and can be used for human bodies. The particularly preferred derivatives include the following compounds of (a) to (m).

(a) Monoglyceride Represented by the Following Formula (II) or (III):

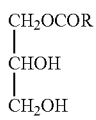
(II)

(III)

In Formula (II) or (III), R represents a linear or branched aliphatic hydrocarbon group having a chain length of an even number of carbon atoms.

(b) Diglyceride Represented by the Following Formula (IV) or (V):

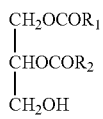
(IV)

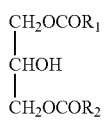
(V)

In Formula (IV) or (V), $R_1$ and $R_2$ are a linear or branched aliphatic hydrocarbon group, and at least one of them represents a linear or branched aliphatic hydrocarbon group having a chain length of an even number of carbon atoms. If either one of $R_1$ and $R_2$ is a linear or branched aliphatic hydrocarbon group having a chain length of an even number of carbon atoms, effects of the present invention are obtained, and the other may be a linear or branched aliphatic hydrocarbon group having a chain length of an odd number of carbon atoms. Further preferably, both of $R_1$ and $R_2$ are linear or branched aliphatic hydrocarbon groups having a chain length of an even number of carbon atoms.

(c) Triglyceride Represented by the Following Formula (VI):

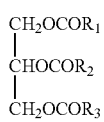
(VI)

In Formula (VI), $R_1$, $R_2$ and $R_3$ are a linear or branched aliphatic hydrocarbon group, and at least one of them represents a linear or branched aliphatic hydrocarbon group having a chain length of an even number of carbon atoms. If at least one of $R_1$, $R_2$ and $R_3$ is a linear or branched aliphatic hydrocarbon group having a chain length of an even number of carbon atoms, effects of the present invention are obtained, and the others may be linear or branched aliphatic hydrocarbon groups having a chain length of an odd number of carbon atoms. Preferably, two or more of $R_1$, $R_2$ and $R_3$ are linear or branched aliphatic hydrocarbon groups having a chain length of an even number of carbon atoms. Further preferably, all of $R_1$, $R_2$ and $R_3$ are linear or branched aliphatic hydrocarbon groups having a chain length of an even number of carbon atoms.

(d) Fatty Acid Salt Represented by the Following Formula (VII):

$$(RCOO)nM \quad (VII)$$

In Formula (VII), R represents a linear or branched aliphatic hydrocarbon group having a chain length of an even number of carbon atoms. M represents a metal atom or an ammonium ion. Further, n represents an integer corresponding to a valency of M.

(e) Ester Represented by the Following Formula (VIII):

$$RCOOR' \quad (VIII)$$

In Formula (VIII), R represents a linear or branched aliphatic hydrocarbon group having a chain length of an even number of carbon atoms. R' represents a monohydric or dihydric aliphatic alcohol residue having an even number of carbon atoms, a polyoxyethylene residue, a sorbitan residue or a sucrose residue.

(f) Primary Amide Represented by the Following Formula (IX):

$$RCONR'R'' \quad (IX)$$

In Formula (IX), R represents a linear or branched aliphatic hydrocarbon group having a chain length of an even number of carbon atoms. R' and R'' represent hydrogen, an alkyl group or a hydroxyalkyl group.

(g) Secondary Amide Represented by the Following Formula (X):

$$R_1CONCOR_2 \\ | \\ R' \quad (X)$$

In Formula (X), $R_1$ and $R_2$ are an aliphatic hydrocarbon group, and either one of them represents a linear or branched aliphatic hydrocarbon group having a chain length of an even number of carbon atoms. R' represents hydrogen, an alkyl group or a hydroxyalkyl group.

(h) Tertiary Amide Represented by the Following Formula (XI):

$$R_1CONCOR_2 \\ | \\ COR_3 \quad (XI)$$

In Formula (XI), $R_1$, $R_2$ and $R_3$ are an aliphatic hydrocarbon group, and at least one of them represents a linear or branched aliphatic hydrocarbon group having a chain length of an even number of a carbon atoms.

(i) Dibasic Acid Represented by the Following Formula (XII) and Salt Thereof:

$$HOOCRCOOH \quad (XII)$$

In Formula (XII), R represents a linear or branched aliphatic hydrocarbon group having a chain length of an odd number of carbon atoms.

(j) Sterol Ester Represented by the Following Formula (XIII):

(XIII) [structure of sterol ester with RCOO— group]

In Formula (XIII), R represents a linear or branched aliphatic hydrocarbon group having a chain length of an even number of carbon atoms.

(k) Phospholipid Represented by the Following Formula (XIV):

$$\begin{array}{l} CH_2OCOR_1 \\ | \\ CHOCOR_2 \\ | \\ CH_2-O\phantom{xx}O^- \\ \phantom{CH_2-O}P \\ \phantom{CH_2-O}O\phantom{xx}X \end{array} \quad (XIV)$$

In Formula (XIV), $R_1$ and $R_2$ are an aliphatic hydrocarbon group, and either one of them represents a linear or branched aliphatic hydrocarbon group having a chain length of an odd number of carbon atoms. X represents a choline residue, an ethanolamine residue, a serine residue or an inositol residue.

(l) Phosphatidic Acid Represented by the Following Formula (XV):

$$\begin{array}{l} CH_2OCOR_1 \\ | \\ CHOCOR_2 \\ | \\ CH_2-O\phantom{xx}O^- \\ \phantom{CH_2-O}P \\ \phantom{CH_2-O}O\phantom{xx}O^- \end{array} \quad (XV)$$

In Formula (XV), $R_1$ and $R_2$ are an aliphatic hydrocarbon group, and either one of them represents a linear or branched aliphatic hydrocarbon group having a chain length of an even number of carbon atoms.

(m) Sphingolipid Represented by the Following Formula (XVI):

$$CH_3(CH_2)_{12}CH=CH-\underset{\underset{OH}{|}}{CH}-\underset{\underset{\underset{R-C=O}{|}}{NH}}{CH}-CH_2-O-X \quad (XVI)$$

In Formula (XVI), R represents a linear or branched aliphatic hydrocarbon group having a chain length of an even number of carbon atoms. X represents a saccharide residue, a phosphoric acid residue or an amine base residue.

In the present invention, the aliphatic alcohol of the component (A) which is preferably used as the hair growth component may have either saturated or unsaturated carbon chain as long as the number of carbon atoms constituting the carbon chain is an odd number. When it is unsaturated, it may contain plural double bonds. Further, the alcohol may be lower alcohol or higher alcohol and may be any of primary, secondary and tertiary alcohols.

Capable of being given as the preferred aliphatic alcohol having an odd number of carbon atoms are, for example, n-propyl alcohol, n-amyl alcohol, n-heptyl alcohol, n-nonyl alcohol, n-undecyl alcohol, n-tridecyl alcohol, n-pentadecyl alcohol, n-heptadecyl alcohol, n-nonadecyl alcohol, n-heneicosyl alcohol, n-tricosyl alcohol and n-pentacosyl alcohol.

Further, the derivatives of the above aliphatic alcohols having an odd number of carbon atoms can be used as well in the present invention. The representative derivatives thereof are esters and ethers of alcohols having an odd number of carbon atoms.

The preferred esters include esters of the aliphatic alcohols having an odd number of carbon atoms described above with aliphatic carboxylic acids (particularly preferably carboxylic acids having 2 to 24 carbon atoms), organic acids such as succinic acid, citric acid, fumaric acid, lactic acid, pyruvic acid, malic acid and oxalacetic acid and inorganic acids such as phosphoric acid.

The preferred ethers include ethers of the aliphatic alcohols having an odd number of carbon atoms described above with aliphatic alcohols (particularly preferably alcohols having 2 to 24 carbon atoms), polyhydric alcohols such as glycerin, polyglycerin, ethylene glycol, propylene glycol and butanediol and saccharides such as fructose, ribose, galactose, arabinose, mannose, xylose, sorbitol and mannitol.

Further, the ethers described above may contain two or more aliphatic alcohol residues having an odd number of carbon atoms in a molecule as is the case with, for example, di- or tri-alkoxides of alcohols having an odd number of carbon atoms of glycerin. The derivatives of the aliphatic alcohols having an odd number of carbon atoms used for the composition of the present invention may only contain the alcohol residues having an odd number of carbon atoms described above as long as they do not exert adverse effects on human bodies. Accordingly, acid residues in the esters described above and alcohol residues and saccharide residues in the ethers may be substituted with various substituents.

The component (A) used in the present invention is preferably glycerin monoesters of fatty acids having an odd number of carbon atoms and includes, to be specific, glyceride of pentadecanoic acid, glyceride of tridecanoic acid and glyceride of heptadecanoic acid, and they provide an excellent hair growth effect.

The compounds selected from the above fatty acids having a chain length of an odd number of carbon atoms or the derivatives thereof and the aliphatic alcohols having a chain length of an odd number of carbon atoms or the derivatives thereof can be used, if necessary, alone or in combination of two or more kinds thereof, and the content thereof is preferably, 0.001 to 20 mass % (hereinafter referred to only as %), particularly preferably, 0.1 to 10% based on the total amount of the hair growth promotor composition.

If the above content of the component (A) is less than 0.001%, the satisfactory hair growth effect is not exhibited in a certain case. On the other hand, if it exceeds 20%, furthermore effects are not usually exhibited.

In Formula (I) representing the component (B) used in the present invention, the group represented by $R_1$ includes the aforementioned respective group, and it is preferably a benzyl group which is non-substituted or has a substituent from the viewpoint of further exhibiting the effects of the present invention. To be specific, it includes a benzyl group, a 2-methylbenzyl group, a 3-methylbenzyl group, a 4-methylbenzyl group, a 4-ethylbenzyl group, a 3-chlorobenzyl group, a 4-chlorobenzyl group, a 2,4-dichlorobenzyl group, a 2-hydroxybenzyl group, a 3-fluorobenzyl group, a 4-nitrobenzyl group, a 4-bromobenzyl group, a 4-fluorobenzyl group, a 3-nitrobenzyl group, a 4-propylbenzyl group, a 3,5-difluorobenzyl group, a 2-cyanobenzyl group, a 2-acetaminobenzyl group, a 4-acetaminobenzyl group, a 4-methoxycarbonylbenzyl group, a 4-dimethylaminobenzyl group, a 4-methoxybenzyl group, a 3-trimethylsilyloxybenzyl group, a 3-trifluoromethylbenzyl group, a 4-butyldimethylsilyloxybenzyl group, a 2-methoxybenzyl group, a 4-trimethylsilyloxybenzyl group and a 4-methylthiobenzyl group.

The group represented by $R_2$ includes preferably, from the viewpoint of further exhibiting the effects of the present invention, a hydrogen atom, pentose (it includes, for example, a 1-ribofuranosyl group, a 1-lyxofuranosyl group, a 1-xylofuranosyl group and a 1-arabofuranosyl group) and hexose (it includes, for example, a 1-glucosyl group, a 1-galactosyl group, a 1-gulose group, a 1-mannosyl-group and a 1-allose group.

The component (B) used in the present invention is the substance represented by Formula (I) described above, and both of the substances obtained by refining a natural product according to an ordinary method and the substance obtained by synthesis can be used.

The specific compound represented by Formula (I) described above which can preferably be used includes 6-benzylaminopurine and the derivatives thereof which are shown below.

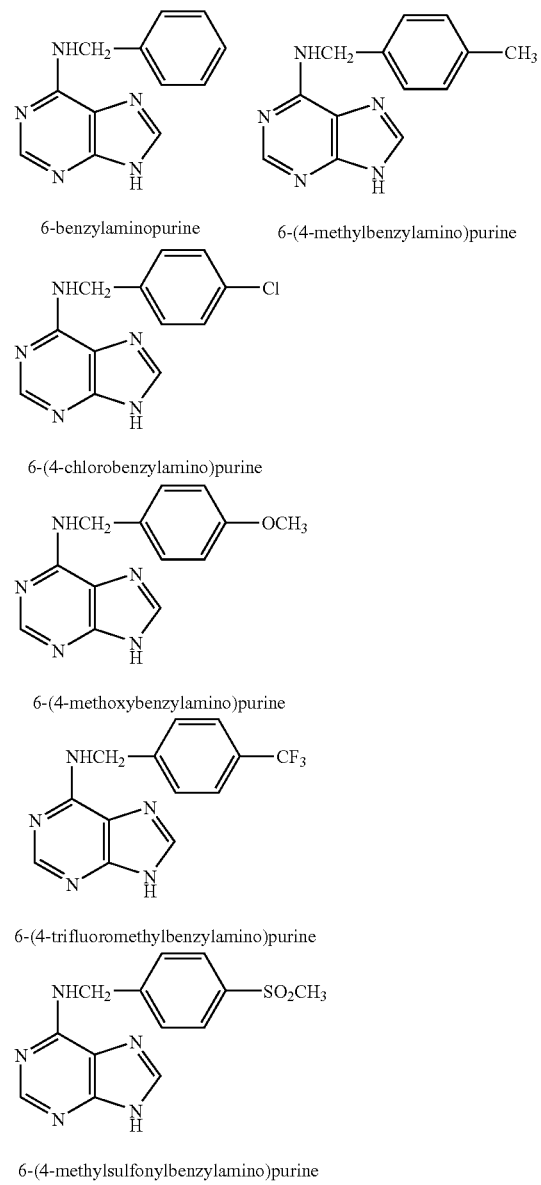

6-benzylaminopurine 6-(4-methylbenzylamino)purine 6-(4-chlorobenzylamino)purine 6-(4-methoxybenzylamino)purine 6-(4-trifluoromethylbenzylamino)purine 6-(4-methylsulfonylbenzylamino)purine -continued

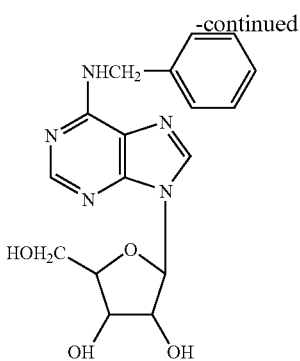

6-benzylamino-9-ribofuranosylpurine

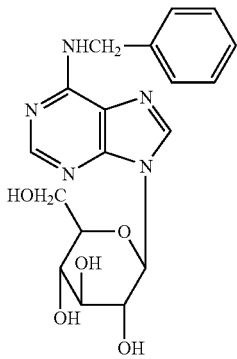

6-benzylamino-9-glucosylpurine

In the present invention, 6-benzylaminopurine represented by Formula (I) and the derivatives thereof can suitably be used alone or in combination of two or more kinds thereof, and they can be added at an optional concentration.

The component (B) is particularly preferably 6-benzylaminopurine and 6-(4-methylbenzylamino)purine from the viewpoint of exhibiting an excellent hair growth effect.

A content of the component (B) used in the present invention is preferably 0.0001 to 10%, more preferably 0.01 to 5% based on the total amount of the hair growth promotor composition.

If the content of the component (B) is less than 0.0001%, the hair growth effect is not sufficiently exhibited in a certain case. On the other hand, if it exceeds 10%, further more effects are not usually exhibited.

In the present invention, the polyglycerin fatty acid ester used as the component (C) shall not be restricted by a polymerization degree of glycerin, a polymerization position of glycerin, a carbon chain length, the presence of unsaturation in the carbon chain, linearity or branching of the carbon chain, the presence of a functional group in the carbon chain and mono-, di-, tri-, or poly-ester. To be specific, it includes triglycerin monolaurate, triglycerin dilaurate, triglycerin monomyristate, triglycerin isostearate, tetraglycerin monooleate, tetraglycerin monocaprate, pentaglycerin monomyristate, pentaglycerin dipalmitate, pentaglycerin monotridecanoate, hexaglycerin diisostearate, hexaglycerin monocondensed recinoleate, hexaglycerin trilaurate, hexaglycerin tetralaurate, heptaglycerin monocaprylate, heptaglycerin trilaurate, heptaglycerin dimyristate, heptaglycerin tristearate, heptaglycerin tetraoleate, decaglycerin monomyristate, decaglycerin monocondensed recinoleate, decaglycerin diisostearate, decaglycerin tetrapentadecanoate, decaglycerin hexaoleate, decaglycerin heptastearate and decaglycerin monorecinoleate, and they can be used alone or in a mixture of two or more kinds thereof.

Among the above polyglycerin fatty acid esters, the esters having a polymerization degree of 3 or more of glycerin are preferred, and the esters having a polymerization degree of 3 to 10 are particularly preferred. If the polymerization degree is 2 or less, the targeted effects are not obtained in a certain case. On the other hand, if the polymerization degree is 11 or more, the raw material is not of a general purpose, and therefore it is not economical in a certain case. To be specific, pentaglycerin monomyristate, decaglycerin monomyristate and pentaglycerin monooleate are suitable.

A content of the polyglycerin fatty acid esters of the component (C) can suitaby be controlled according to the contents of the component (A) and the component (B) each described above, and it is preferably 0.001 to 10%, particularly preferably, 0.01 to 5% based on the total amount of the hair growth promotor composition.

If the content of the component (C) is less than 0.001%, the targeted stabilization effect at low temperature is not sufficiently exhibited in a certain case. On the other hand, if it exceeds 10%, further more effects are not usually exhibited.

In the present invention, the sorbitan fatty acid ester used as the component (D) shall not be restricted by a carbon chain length, the presence of unsaturation in the carbon chain, linearity or branching of the carbon chain and mono-, di-, tri-, or poly-ester, and it includes, to be specific, sorbitan monolaurate, sorbitan monostearate, sorbitan tristearate, sorbitan monoisostearate, sorbitan monooleate and sorbitan sesquioleate. They can be used alone or in a mixture of two or more kinds thereof.

Among the above components (D), the fatty acid monoesters of sorbitan are preferred and include, to be specific, sorbitan coconut oil fatty acid ester and sorbitan monolaurate.

A content of the sorbitan fatty acid esters of the component (D) is preferably 0.001 to 10%, particularly preferably, 0.01 to 5% based on the total amount of the hair growth promotor composition.

If the content of the component (D) is less than 0.001%, the stabilization effect at low temperature is not sufficiently exhibited in a certain case. On the other hand, if it exceeds 10%, further more effects are not usually exhibited, and an adverse effect such as stickiness is exerted on the use feeling.

In the present invention, the hair growth promotor composition which contains, as the essential components, a compound of the component (A) described above and at least one selected from 6-benzylaminopurine and/or the derivatives thereof represented by Formula (I) described above, which is the component (B) and which are further contains the polyglycerin fatty acid ester of the component (C) described above and the sorbitan fatty acid ester of the component (D) described above, whereby obtained is the hair growth promotor composition which exhibits a particularly excellent hair growth effect and in which active ingredients are stable over a long period of time and practicality is high, and the essential components can be added at optional concentrations.

Further, the content proportions in which a synergistic effect of the constitutional substances described above contained in the hair growth promotor composition is exerted to a maximum extent have been investigated to result in finding that a mass ratio of component (C)/component (D) is preferably 10/1 to 1/60, more preferably 5/1 to 1/10.

The targeted stabilization effect at low temperature can be exhibited to a maximum extent by controlling a mass ratio of component (C)/component (D) to 10/1 to 1/60.

Since the hair growth promotor composition of the present invention is an ethanol or aqueous ethanol preparation, it can contain, in addition to the component (A) to the component (D) each described above, ethanol (fermented ethanol, synthesized ethanol, denatured ethanol and the like) and water (refined water, distilled water, ion-exchanged water, purified water, ultrapure water and the like) as the balance. In addition to the respective components described above, it may contain optional components according to the use purposes thereof. Capable of being given as such components are, for example, nonionic surfactants, glucide base surfactants, other surfactants, celluloses, oils & fats, ester oils, high molecular resins, coloring agents, fragrances, UV absorbers and medicinal components such as vitamins, hormones, vasodilator agents, amino acids, antiinflammatory agents, cutaneous function accelerators and keratorytic drugs.

The celluloses include hydroxymethyl cellulose, hydroxypropyl cellulose and hydroxypropylmethyl cellulose; the surfactants include polyoxyethylene-hardened castor oil, polyoxyethylene-hardened castor oil monostearate and glycerin fatty acid esters; the oils & fats include polyhydric alcohol fatty acid esters (glycerin tri-2-ethylhexanoate, trimethylpropa ne tri isostearate, and the like), safflower oil, evening primrose oil and jojoba oil; the ester oils include unsaturated fatty acid alkyl esters (ethyl oleate, isopropyl linoleate and the like), methyl myristate and isopropyl myristate; the amino acids include methionine, serine, glycine and cystine; the keratorytic drugs include salicylic acid and resorcin; the high molecular resins include amphoteric, cationic, anionic and nonionic polymers; and the UV absorbers include octyl methoxycinnamate (Neoheliopan AV), oxybenzone and urocanic acid.

The hair growth promotor composition of the present invention can be used as an external preparation in the form of a homogeneous solution, a lotion and a gel. The hair growth promotor composition of the present invention can assume the form of an aerosol composition, and in such case, it can contain, in addition to the components described above, lower alcohols such as n-propyl alcohol and isopropyl alcohol, combustible gases such as butane, propane, isobutane, liquefied petroleum gas and dimethyl ether and compressed gases such as nitrogen gas, oxygen gas, carbon dioxide gas and nitrous oxide gas.

In the hair growth promotor composition of the present invention thus constituted, an excellent hair growth effect is obtained by combined use of at least one compound selected from the fatty acids having a chain length of an odd number of carbon atoms, the derivatives of said fatty acids, the aliphatic alcohols having a chain length of an odd number of carbon atoms and the derivatives of said aliphatic alcohols with 6-benzylaminopurine and/or the derivatives thereof, and reduction in stability at low temperature and use feeling caused by the combined use described above are improved without damaging the hair growth effect described above by further adding at least one of polyglycerin fatty acid esters and at least one of sorbitan fatty acid esters.

EXAMPLES

Next, the present invention shall be explained in further detail with reference to examples and comparative examples, but the present invention shall not be restricted to the examples described below.

Examples 1 to 8 and Comparative Examples 1 to 7

The respective hair growth promotor compositions were prepared according to formulations shown in the following Table 1 and Table 2. The blend unit is mass %, and the total amount is 100 mass % (the same shall apply to Example 9 and examples subsequent thereto).

The hair growth promotor compositions (samples to be tested falling in the scope of the present invention (examples) and samples to be tested falling outside the scope of the present invention (comparative examples)) thus obtained were evaluated for a hair growth effect, use feeling and stability at a low temperature by the respective methods described below. The results thereof are shown in Table 1 and Table 2.

Evaluation Method of Hair Growth Effect:

The volunteers of 64 adult men were divided at random into total 8 groups as a subject group and a control group, in which one group consists of 8 men.

The test was carried out by applying adequate amounts of the compositions onto a frontal region through a parietal region twice a day, in the morning and at night. The administration period was 4 months.

An improvement degree of the hairs at the time of finishing the test (4 months) as compared with those before starting the test was judged according to the following five stage evaluation (notable improvement, middle improvement, light improvement, unchanged and degraded) referring to observation of the photos.

Judgment Criteria:

notable improvement: vellus hairs were scarcely observed and normalized middle improvement: vellus hairs were turned to terminal hairs to a considerable extent light improvement: vellus hairs were slightly turned to terminal hairs unchanged: change was not observed at all on the quality of the hairs degraded: the hairs were turned to vellus hairs.

The evaluation results of the hair growth effect shown in Table 1 and Table 2 were shown by a proportion (%, improvement rate) of the number of the persons having the effects of notable improvement~light improvement after used respectively by 8 persons.

Evaluation Method of Use Feeling:

The use feeling (average) in evaluating the hair growth-accelerating effect described above, that is, in applying the adequate amount onto a frontal region through a parietal region twice a day, in the morning and at night, was evaluated according to the following evaluation criteria.

Evaluation Criteria:

○: hairs are not dried up, and good use feeling is obtained

Δ: hairs are dried up a little, but use feeling is not dissatisfactory

X: hairs are dried up, and use feeling is dissatisfactory

Evaluation Method of Stability at Low Temperature:

A transparent glass bottle having a cap was filled with about 50 mL of the respective samples obtained and then stored at −10° C. to evaluate deposition of crystals and the presence of precipitates with eyes after 4 weeks according to the following evaluation criteria.

Evaluation Criteria:

○: crystals and precipitates are not observed

Δ: trace amounts of crystals and precipitates are observed

X: crystals or precipitates are observed

TABLE 1

| | | Blend amount (%) Example | | | | | | | |
|---|---|---|---|---|---|---|---|---|---|
| | | 1 | 2 | 3 | 4 | 5 | 6 | 7 | 8 |
| Component (A) | Glycerin tridecanoate | 2.0 | 2.0 | 2.0 | | | | 2.0 | |
| | Glycerin pentadecanoate | | | | 2.0 | 2.0 | 2.0 | | 2.0 |
| Component (B) | 6-Benzylamino-Purine | 0.5 | 0.5 | | 0.5 | | | | 0.5 |
| | 6-(4-Methylbenzylamino)purine | | | 0.5 | | 0.5 | 0.5 | 0.5 | |
| Component (C) | Pentaglycerin monomyristate | 0.5 | | | 1.0 | | | 0.05 | |
| | Decaglycerin monomyristate | | 0.5 | | | | 2.0 | | 0.05 |
| | Pentaglycerin monooleate | | | 1.0 | | | 2.0 | | |
| Component (D) | Sorbitan monolaurate | 3.0 | 3.0 | 3.0 | 3.0 | 3.0 | 3.0 | 3.0 | 3.0 |
| 99% ethanol | | Balance | Balance | Balance | Balance | Balance | Balance | Balance | Balance |
| Evaluation of hair growth effect | | 75 | 75 | 63 | 75 | 75 | 75 | 63 | 63 |
| Evaluation of use feeling | | ○ | ○ | ○ | ○ | ○ | ○ | Δ | Δ |
| Evaluation of stability at low temperature | | ○ | ○ | ○ | ○ | ○ | ○ | ○ | ○ |

TABLE 2

| | | Blend amount (%) Comparative Example | | | | | | |
|---|---|---|---|---|---|---|---|---|
| | | 1 | 2 | 3 | 4 | 5 | 6 | 7 |
| Component (A) | Glycerin tridecanoate | 2.0 | 2.0 | 2.0 | | | | |
| | Glycerin pentadecanoate | | | | 2.0 | 2.0 | 2.0 | 2.0 |
| Component (B) | 6-Benzylamino-purine | 0.5 | 0.5 | | | | | 0.5 |
| | 6-(4-Methylbenzylamino)purine | | | 0.5 | 0.5 | 0.5 | 0.5 | |
| Component (C) | Pentaglycerin monomyristate | | 2.0 | | | | | |
| | Decaglycerin monomyristate | | | | 2.0 | | | |
| | Pentaglycerin monooleate | | | | | | | 2.0 |
| Component (D) | Sorbitan monolaurate | | | 3.0 | | | 1.0 | |
| 99% ethanol | | Balance | Balance | Balance | Balance | Balance | Balance | Balance |
| Evaluation of hair growth effect | | 75 | 75 | 63 | 75 | 75 | 75 | 63 |
| Evaluation of use feeling | | X | Δ | ○ | Δ | X | ○ | Δ |
| Evaluation of stability at low temperature | | X | X | X | X | X | X | X |

As apparent from the results shown in Table 1 and Table 2, it has become clear that in all of Examples 1 to 8 containing the prescribed amounts of the active ingredients (the component (A) to the component (D)) falling in the scope of the present invention, excellent characteristics are shown in the hair growth effect, the use feeling and the stability at low temperature and that in all of Comparative Examples 1 to 7 falling outside the scope of the present invention, excellent characteristics are not shown in the use feeling and the stability at low temperature.

To specifically observe the comparative examples, Comparative Examples 1 and 5 are cases in which the component (A) and the component (B) are contained and both of the component (C) and the component (D) are not contained, and Comparative Examples 2 to 4, 6 and 7 are cases in which the component (A) and the component (B) are contained and either one of the component (C) and the component (D) is contained. It can be found that the effects of the present invention can not be exhibited in the above cases.

Examples 9 to 20

Next, examples in which the hair growth promotor compositions of the present invention have been applied to commercial products shall be shown. The hair growth promotor compositions in the respective examples described below were prepared according to the respective formulations by ordinary methods for preparing the respective preparations.

The hair growth promotor compositions of various preparations (a hair growth promotor, a hair growth spray, a hair growth tonic and a hair growth lotion) prepared in Examples 9 to 20 described below were evaluated for a hair growth effect, use feeling and stability at low temperature in the same manners as in Examples 1 to 8 to find that the same excellent effects as in Example 1 were shown in all examples.

Example 9

Hair Growth Promotor

| Formulation | |
|---|---|
| Glycerin monopentadecanoate | 3.0 |
| 6-Benzylaminopurine | 0.5 |
| DL-α-tocopheryl acetate | 0.1 |
| *Coleus•forskohlii* root extract | 0.5 |
| Glycerin | 0.5 |
| Sorbitan coconut oil fatty acid ester | 1.0 |
| Sucrose myristic acid ester | 0.5 |
| Decaglycerin monomyristate | 1.0 |
| Lauryldimethylamino acetic acid betaine | 0.3 |
| Amphoteric polymer* | 0.2 |
| Ethyl oleate | 2.0 |
| Succinic acid | 0.1 |
| Fragrance# | 0.5 |
| Refined water | 0.3 |
| 99.5% ethanol | balance |

*N-methacryloylethyl-N,N-dimethylammonium-α-N-methylcarboxybetaine•alkyl methacrylate copolymer
an A composition in Table 2 described in Japanese Patent Application Laid-Open No. 113019/2003

Example 10

Hair Growth Promotor

| Formulation | |
|---|---|
| Glycerin monopentadecanoate | 2.0 |
| 6-Benzylaminopurine | 0.1 |
| β-glycyrrhetic acid | 0.1 |
| Amphoteric polymer* | 0.2 |
| Ethyl oleate | 1.0 |
| Succinic acid | 0.3 |
| Sucrose lauric acid ester | 0.5 |
| Sorbitan monolaurate | 0.5 |
| Glycerin | 0.8 |
| Decaglycerin monomyristate | 0.5 |
| L-menthol | 0.1 |
| DL-α-tocopheryl acetate | 0.1 |
| Refined water | 0.3 |
| Fragrance# | 0.5 |
| 99.5% ethanol | balance |
| Prepared fluid | |
| Formulated concentrate described above | 80% |
| LPG | 20% |

*N-methacryloylethyl-N,N-dimethylammonium-α-N-methylcarboxybetaine•alkyl methacrylate copolymer
a B composition in Table 2 described in Japanese Patent Application Laid-Open No. 113019/2003

Example 11

Hair Growth Tonic

| Formulation | |
|---|---|
| Glycerin monopentadecanoate | 2.0 |
| 6-Benzylaminopurine | 0.05 |
| POE (8 mole) oleyl ether | 1.5 |
| Sorbitan monomyristate | 3.0 |
| Pentaglycerin monolaurate | 0.3 |
| L-menthol | 0.1 |
| Hinokitiol | 0.3 |
| Methylparaben | 0.1 |
| Fragrance# | 0.3 |
| Refined water | 0.3 |
| 99.5% ethanol | balance | a C composition in Table 2 described in Japanese Patent Application Laid-Open No. 113019/2003

Example 12

Hair Growth Lotion

| Formulation | |
|---|---|
| Glycerin monopentadecanoate | 1.0 |
| 6-(4-Methylbenzylamino)purine | 0.5 |
| Natural vitamin E | 0.5 |
| Sucrose myristic acid ester | 0.5 |
| POE (40) hardened castor oil | 0.5 |
| Pentaglycerin monooleate | 0.5 |
| Sorbitan monomyristate | 0.8 |
| Citric acid | 0.1 |
| L-menthol | 0.1 |
| Fragrance# | 0.5 |
| Refined water | 0.3 |
| 99.5% ethanol | balance | a D composition in Table 2 described in Japanese Patent Application Laid-Open No. 113019/2003

Example 13

Hair Growth Promotor

| Formulation | |
|---|---|
| Glycerin monopentadecanoate | 3.0 |
| 6-Benzylaminopurine | 0.4 |
| D-pantothenyl alcohol | 0.4 |
| β-glycyrrhetic acid | 0.1 |
| Pyrocton olamin | 0.1 |
| Gallic acid 3,5-diglucoside | 0.1 |
| Pentaglycerin monooleate | 0.8 |
| *Coleus* extract | 1.2 |
| Stearyltrimethylammonium chloride | 0.8 |
| Sorbitan monolaurate | 0.5 |
| Lauryldimethylamino acetic acid betaine | 0.3 |
| Amphoteric polymer* | 0.2 |
| Ethyl oleate | 2.0 |
| Succinic acid | 0.1 |
| Fragrance# | 0.5 |
| Refined water | 0.3 |
| 99.5% ethanol | balance |

*N-methacryloylethyl-N,N-dimethylammonium-α-N-methylcarboxybetaine•alkyl methacrylate copolymer
an A composition in Table 2 described in Japanese Patent Application Laid-Open No. 113019/2003

Example 14

Hair Growth Promotor

| Formulation | |
|---|---|
| Glycerin monopentadecanoate | 3.0 |
| 6-Benzylaminopurine | 0.4 |
| Nicotinamide | 0.4 |

-continued

| Formulation | |
|---|---|
| β-glycyrrhetic acid | 0.1 |
| Pyrocton olamin | 0.1 |
| Gallic acid-3,5-diglucoside | 0.1 |
| Methyl salicylate | 0.5 |
| Sorbitan monooleate | 3.0 |
| Decaglycerin monomyristate | 0.5 |
| Stearyltrimethylammonium chloride | 0.4 |
| Polyoxyethylene oleyl ether | 0.5 |
| Lauryldimethylamino acetic acid betaine | 0.3 |
| Amphoteric polymer* | 0.2 |
| Polyethylene glycol | 2.0 |
| L-menthol | 0.1 |
| Fragrance# | 0.2 |
| Succinic acid | 0.1 |
| Ethanol | balance |

*N-methacryloylethyl-N,N-dimethylammonium-α-N-methylcarboxybetaine•alkyl methacrylate copolymer
a C composition in Table 2 described in Japanese Patent Application Laid-Open No. 113019/2003

Example 15

Hair Growth Promotor

| Formulation | |
|---|---|
| Glycerin monopentadecanoate | 3.0 |
| 6-Benzylaminopurine | 0.4 |
| Nicotinamide | 0.4 |
| Tocopheryl acetate | 0.1 |
| Pyrocton olamin | 0.1 |
| Gallic acid-3,5-diglucoside | 0.05 |
| Propylene glycol | 6.0 |
| Stearyltrimethylammonium chloride | 0.6 |
| Decaglycerin monomyristate | 0.5 |
| Sorbitan monolaurate | 5.0 |
| Polyoxyethylene oleyl ether | 0.5 |
| Polyethylene glycol | 2.0 |
| L-menthol | 0.2 |
| Nylon powder*1 | 1.5 |
| Fragrance# | 0.2 |
| Ethanol | balance |

*1nylon 12, average particle diameter: about 10 μm
a B composition in Table 2 described in Japanese Patent Application Laid-Open No. 113019/2003

Example 16

Hair Growth Promotor

| Formulation | |
|---|---|
| 6-Benzylaminopurine | 0.5 |
| Glycerin monopentadecanoate | 3.0 |
| Gallic acid-3,5-diglucoside | 0.3 |
| Tocopheryl acetate | 0.1 |
| Sorbitan palmitate | 2.0 |
| β-glycyrrhetic acid | 0.5 |
| Sorbitan coconut oil fatty acid ester | 0.5 |
| Stearyltrimethylammonium chloride | 0.3 |
| Sucrose fatty acid ester | 0.3 |
| Decaglycerin monomyristate | 0.6 |
| Amphoteric polymer* | 0.02 |
| Ethyl oleate | 1.5 |

-continued

| Formulation | |
|---|---|
| Pantothenyl ethyl ether | 1.0 |
| D-pantothenyl alcohol | 1.0 |
| Coleus•forskohlii root extract | 2.0 |
| Conc. glycerin | 1.0 |
| Isodonis Japonicus extract | 1.0 |
| Succinic acid | 0.1 |
| Benzalkonium chloride | 0.02 |
| L-menthol | 0.1 |
| Ethanol | balance |

*N-methacryloylethyl-N,N-dimethylammonium-α-N-methylcarboxybetaine•alkyl methacrylate copolymer Example 17

Hair Growth Promotor

| Formulation | |
|---|---|
| 6-Benzylaminopurine | 0.5 |
| Glycerin monopentadecanoate | 3.0 |
| Tocopheryl acetate | 0.1 |
| Sorbitan coconut oil fatty acid ester | 2.0 |
| Sucrose fatty acid ester | 0.3 |
| Decaglycerin monomyristate | 0.6 |
| Amphoteric polymer* | 0.5 |
| Ethyl oleate | 1.5 |
| Coleus•forskohlii root extract | 1.5 |
| Glycerin | 1.0 |
| Glycerin monomyristate | 0.05 |
| Pentadecanoic acid | 0.01 |
| Myristic acid | 0.01 |
| Glycerin dipentadecanoate | 0.05 |
| Succinic acid | 0.1 |
| L-menthol | 0.1 |
| Fragrance# | 0.2 |
| Ethanol | balance |

*N-methacryloylethyl-N,N-dimethylammonium-α-N-methylcarboxybetaine•alkyl methacrylate copolymer
a C composition in Table 2 described in Japanese Patent Application Laid-Open No. 113019/2003

Example 18

Hair Growth Promotor

| Formulation | |
|---|---|
| 6-Benzylaminopurine | 0.5 |
| Glycerin monopentadecanoate | 2.0 |
| Tocopheryl acetate | 0.1 |
| β-glycyrrhetic acid | 0.1 |
| Sorbitan palmitate | 2.0 |
| Sorbitan coconut oil fatty acid ester | 0.5 |
| Sucrose fatty acid ester | 0.3 |
| Decaglycerin monomyristate | 0.6 |
| Amphoteric polymer* | 0.02 |
| Ethyl oleate | 1.5 |
| Pantothenyl ethyl ether | 1.0 |
| Coleus•forskohlii root extract | 2.0 |
| Pentadecanoic acid | 0.05 |
| Palmitic acid | 0.01 |
| Glycerin monopalmitate | 0.02 |
| Glycerin dipentadecanoate | 0.05 |
| Glycerin | 0.03 |

-continued

| Formulation | |
|---|---|
| *Isodonis Japonicus* extract | 1.0 |
| Succinic acid | 0.1 |
| L-menthol | 0.2 |
| Fragrance# | 0.2 |
| Ethanol | balance |

*N-methacryloylethyl-N,N-dimethylammonium-α-N-methylcarboxybetaine•alkyl methacrylate copolymer
a D composition in Table 2 described in Japanese Patent Application Laid-Open No. 113019/2003

Example 19

Hair Growth Promotor

| Formulation | |
|---|---|
| 6-Benzylaminopurine | 0.5 |
| Glycerin monopentadecanoate | 3.0 |
| Tocopheryl acetate | 0.1 |
| Gallic acid-3,5-diglucoside | 0.3 |
| Sorbitan coconut oil fatty acid ester | 2.0 |
| Sucrose fatty acid ester | 0.3 |
| Ethyl oleate | 1.5 |
| Decaglycerin monomyristate | 0.6 |
| Amphoteric polymer* | 0.5 |
| Stearyltrimethylammonium chloride | 0.3 |
| Coleus•forskohlii root extract | 1.5 |
| Glycerin | 1.0 |
| Pentadecanoic acid | 0.01 |
| Myristic acid | 0.01 |
| Glycerin monomyristate | 0.05 |
| Glycerin dipentadecanoate | 0.05 |
| Succinic acid | 0.1 |
| L-menthol | 0.1 |
| Fragrance# | 0.2 |
| Ethanol | balance |

*N-methacryloylethyl-N,N-dimethylammonium-α-N-methylcarboxybetaine•alkyl methacrylate copolymer
an E composition in Table 2 described in Japanese Patent Application Laid-Open No. 113019/2003

Example 20

Hair Growth Promotor Spray

| Formulation | |
|---|---|
| 6-Benzylaminopurine | 0.5 |
| Glycerin monopentadecanoate | 3.0 |
| Tocopheryl acetate | 0.1 |
| Gallic acid-3,5-diglucoside | 0.3 |
| Sorbitan coconut oil fatty acid ester | 2.0 |
| Sucrose fatty acid ester | 0.3 |
| Ethyl oleate | 1.5 |
| Decaglycerin monomyristate | 0.6 |
| Amphoteric polymer* | 0.5 |
| Stearyltrimethylammonium chloride | 0.3 |
| Coleus•forskohlii root extract | 1.5 |
| Glycerin | 1.0 |
| Pentadecanoic acid | 0.01 |
| Myristic acid | 0.01 |
| Glycerin monomyristate | 0.05 |
| Glycerin dipentadecanoate | 0.05 |
| Succinic acid | 0.1 |
| L-menthol | 0.1 |
| Fragrance# | 0.2 |
| Ethanol | balance |
| Prepared fluid | |
| Formulated concentrate described above | 80% |
| LPG | 20% |

*N-methacryloylethyl-N,N-dimethylammonium-α-N-methylcarboxybetaine•alkyl methacrylate copolymer
an E composition in Table 2 described in Japanese Patent Application Laid-Open No. 113019/2003

INDUSTRIAL APPLICATION

The hair growth promotor composition of the present invention thus constituted exhibits an excellent hair growth effect by applying externally onto a scalp and is excellent in stability at low temperature, and it provides good use feeling having no stickiness, so that the hair growth promotor composition having excellent effects which have not so far been shown is provided.

What is claimed is:

1. A hair growth promotor which is an ethanol or aqueous ethanol preparation comprising, as active ingredients for a hair grown promoter, (A) at least one compound selected from fatty acids having a chain length of an odd number of carbon atoms, the derivatives of the fatty acids, aliphatic alcohols having a chain length of an odd number of carbon atoms and the derivatives of the aliphatic alcohols and (B) at least one selected from 6-benzylaminopurine and/or the derivatives thereof represented by the following Formula (I), wherein it further comprises (C) at least one of polyglycerin fatty acid esters in which the polyglycerin has a polymerization degree of 3 to 10 of glycerin and (D) at least one of sorbitan fatty acid esters:

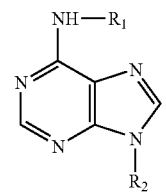

(I)

in Formula (I) $R_1$ is an alkyl group having 1 to 22 carbon atoms, a cyclic hydrocarbon group, an alkenyl group having 1 to 22 carbon atoms, an aralkyl group which is non-substituted or has a substituent, a styryl group which is non-substituted or has a substituent, an alkylamino group, an amino group having a cyclic hydrocarbon group, an alkenylamino group, a benzylamino group which is non-substituted or has a substituent, a phenylethylamino group which is non-substituted or has a substituent, a phenylamino group which is non-substituted or has a substituent, a phenylaminocarbonylamino group which is non-substituted or has a substituent, a pyridylamino group, a pyridylmethylamino group, a pyrrolylmethylamino group, an oxazolylmethylamino group, an imidazolylmethylamino group, a pyridazolylmethylamino group, a naphthylamino group or a naphthylmethylamino group, and $R_2$ is a hydrogen atom, a pentose or hexose.

* * * * *